United States Patent [19]

Hughes et al.

[11] 4,242,291

[45] Dec. 30, 1980

[54] COLLAGEN RECONSTITUTION

[75] Inventors: Kenneth E. Hughes, Gahanna; Dale P. DeVore, Worthington, both of Ohio

[73] Assignee: Battelle Development Corporation, Columbus, Ohio

[21] Appl. No.: 37,551

[22] Filed: May 9, 1979

[51] Int. Cl.³ .......................... C07G 7/00; B29D 11/00
[52] U.S. Cl. ..................................... 264/1; 260/123.7; 264/153; 351/160 H
[58] Field of Search .......................... 351/160, 160 H; 260/123.7; 264/1, 202, 153

[56] References Cited

U.S. PATENT DOCUMENTS

| 3,075,961 | 1/1963 | Veis et al. | 260/117 |
| 3,553,299 | 1/1971 | Thiele et al. | 264/1 |
| 3,676,298 | 7/1972 | Moczar et al. | 351/160 H |

FOREIGN PATENT DOCUMENTS

| 49-39174 | 10/1974 | Japan | 264/1 |
| 51-14035 | 2/1976 | Japan | 351/160 H |
| 51-30749 | 3/1976 | Japan | 351/160 H |

*Primary Examiner*—Jay H. Woo
*Attorney, Agent, or Firm*—Barry S. Bissell

[57] ABSTRACT

The effect of earth gravity on the self assembly of tropocollagen molecules into collagen fibrils and on the aggregation of fibrils into collagen gels has been found to be surprisingly detrimental to the preparation of desirable biomaterials. Chemically and physically uniform biomaterials for use in repair or replacement of damaged or diseased human tissue and organs are prepared by otherwise conventional reconstitution of soluble tropocollagen carried out, however, under less than one gravity, preferably under zero gravity. Surprisingly better properties of the collagen aggregate suggest that improved biomaterials may be prepared from the uniform gels.

7 Claims, 3 Drawing Figures

COLLAGEN RECONSTITUTION

BACKGROUND OF THE INVENTION

Fibrillogenesis or reconstitution of soluble tropocollagen into native collagen fibers and aggregate is well known in the art. For example, U.S. Pat. No. 3,075,961 describes one method for reconstituting collagen from acid precursor gelatin. Volume 5 of the *Molecular Biology* series entitled "The Macromolecular Chemistry of Gelatin" by Arthur Veis (1964) also describes in detail the production and processing of collagen.

SUMMARY OF THE INVENTION

It is an object of the present invention to provide an improved process for the reconstitution of soluble collagen molecules into homogeneous collagen gels or aggregate.

It is a further object to provide an improved method for the production of uniform collagen biomaterials for repair and replacement of human tissue and organs.

In accordance with the objectives, the invention is an improved method of producing a reconstituted collagen gel from a solution of solubilized tropocollagen molecules wherein a homogeneous collagen gel matrix is precipitated from the solution under gravitational force of less than one gravity. Preferably, the gravitational force is about zero gravity.

The invention further comprises performing the improved process within or on a die or mold whereby a homogeneous collagen biomaterial device is obtained. For example, an eye lense prosthesis (an artifical cornea, contact lens or interocular lens for the eye) may be formed directly if the improved method is carried out in an eye lense mold or die. Moreover, biomaterial parts can be fabricated from gel sheets made by the process and may be further shaped, for example by cutting, abrading, heating and chemical treatment.

Additives or impurities to selectively alter material properties may also be incorporated into the homogeneous reconstituted collagen matrix by introducing the additive into the solution prior to fibrillogenesis.

DETAILED DESCRIPTION OF THE INVENTION

Figure 1:
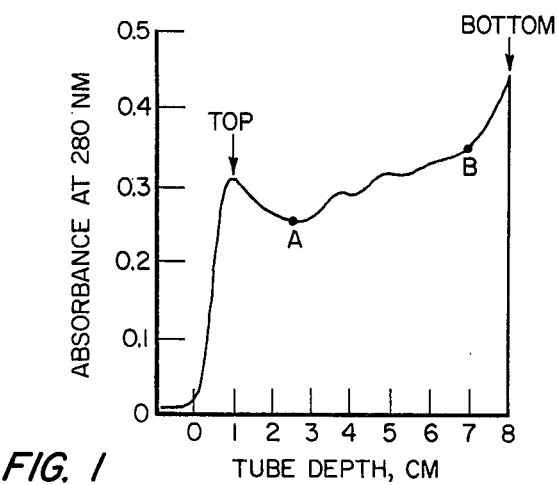
FIG. 1 and FIG. 2 are graphs of absorbence as a function of position of a collagen gel reconstituted at one gravity in a tube.

Collagen is the principal proteinaceous component of the white fibrous connective tissue. Collagen comprises about 30% of the organic matter in mammals and nearly 60% of the protein content. Because of this varied utilization of collagen, the fibers in various tissue are organized in different ways, are produced from different types of cells and are associated with various other substances. Thus purity and structure are important properties of the collagen fibers in respect of their ultimate use and suitability. The present invention proposes to improve the structure of reconstituted collagen fibrils and aggregate by processing under reduced gravity environment. Because of its compatibility with body tissue, the reconstituted collagen is useful in making replacement tissue and body organs. The homogeneous collagen gel produced by the present improved fibrillogenesis process is expected to result in vastly improved biomaterials for such replacement.

Reconstitution of insoluble collagen fibrils as known in the art comprises the steps of, (1) dissolving the soluble collagen molecules from any collagen source, for example, the tissue of young animals, (2) separating and purifying the soluble collagen molecules, and (3) precipitating and recovering the reconstituted collagen gel matrix by inducing a "polymerization" of the soluble molecules into insoluble collagen fibrils and subsequent three dimensional organization by unit assembly of the collagen fibrils into the collagen gel matrix.

The individual soluble collagen molecules extracted from animal tissue are primarily macromolecular monomer units known as tropocollagen (collagen-former). These tropocollagen units have a three chain helix structure and are on the order of 2800 Å in length and 15 Å in diameter. The insoluble collagen fibrils grow from these tropocollagen molecules which are caused to join in staggered layers by an exogenous change in the environment, for example, by a change in pH or temperature of the solution. The collagen fibrils then aggregate into a gel matrix by unit assembly and possible crosslinking.

Since lyophilized tropocollagen is commercially available, it would be possible to reconstitute collagen fibrils by merely redissolving the lyophilized tropocollagen and precipitating the collagen fibrils. However, the purity of available tropocollagen is somewhat less than that which can be produced in the laboratory, and we prefer to extract and purify the tropocollagen. Moreover, the extraction and purification can be customized in the laboratory such that certain desired "impurities" from the collagen source may be selectively retained with the tropocollagen to produce a reconstituted collagen with particular properties. Alternatively, additives such as complex carbohydrates (e.g. mucopolysaccharides), salts (e.g., $CaPO_4$), proteoglycans, or other proteins (e.g., elastin), can be added to the soluble tropocollagen to be incorporated into the precipitated collagen gel resulting in the optimization of certain properties such as strength or flexibility.

EXTRACTION

The preferred process of extracting and purifying tropocollagen is as follows. A source of collagen such as rat tail tendon or young animal skin is cleaned, cut up into small pieces and placed in an acid extracting solution. Acetic, citric, glycolic and propionic are examples of the acids which may be used as the extractant.

Tropocollagen, being soluble in acid solution, is dissolved along with other soluble impurities. Agitation over two or three days may be required to solubilize the tropocollagen.

Separation is accomplished by filtering and centrifugation, after which the supernatant contains the tropocollagen. The supernatant is recovered and tropocollagen is then precipitated therefrom by raising the pH with a NaCl solution. The tropocollagen is finally recovered by centrifuging the solution.

Purification of the recovered tropocollagen begins by redissolving in acetic acid and then salting out. This may be repeated several times at different pH. Subsequently, the salt is dialyzed out of the tropocollagen in an acid bath. At this point, the tropocollagen may be further purified by ultracentrifugation and the supernatant of pure collagen may be directly used in fibrillogenesis or may be lyophilized and stored at −20° C. until needed.

In addition to acid extraction, a larger percentage of collagen may also be extracted by an enzyme treatment. The collagen removed by this method will also be defined for purposes of this invention as tropocollagen, although it is a slightly different form than that removed during acid extraction.

In the enzyme method, the source of collagen is washed with, for example, Proctase, a proteolytic enzyme with a pH optimum of about 3.0. The treatment results in the solubilization of large amounts of acid insoluble collagen and the digestion of non-collagenous protein contaminants. Insoluble material is removed by centrifugation and the collagen is precipitated and treated again with Proctase. The collagen is again precipitated by dialysis against a dibasic sodium phosphate or by neutralization with sodium hydroxide followed by further purification by repeated salt precipitation and solubilization in acid. The final precipitate is dissolved in 0.05% acetic acid and ultracentrifuged at 100,000 gravity forces for several hours to remove sediment. The resulting clear supernatant may be passed through a 0.4 micron Millipore filter and lyophilized for storage.

RECONSTITUTION

The fibrillogenesis is preferably induced in dilute acid solution (e.g., 0.05 M acetic acid) of tropocollagen by a combination of pH and temperature. Passage of electric current or irradiation with ultraviolet light could also be used. At temperatures above about 4° C. and pH in the range of 5.5-8.0, the collagen fibrils can grow. However, introduction of a salt solution into room temperature tropocollagen solution would cause localized, disruptive fiber formation. The preferred method is to dialyze the acetic-acid solution of tropocollagen at about 4° C. in a neutral buffer solution. The tris buffer has been used with an addition of NaCl, NaOH and/or $Na_2PO_4$. When the molecules are equilibrated with buffer at 4° C., the temperature may then be gradually raised to room temperature causing spontaneous well-ordered fibril formation and subsequent aggregation of collagen gel.

The present invention proposes to carry out the above fibril formation from the acid tropocollagen solution under gravitational force less than one gravity. Preferably, the fibrillogensis is carried out under about zero gravity. A gradual improvement in fibril properties is expected between one and zero gravity, however for purposes of definition, we prefer that "about zero gravity" means less than about one-tenth of earth gravity. The improved process is preferably carried out in space.

Conventional formation of fibrils from the tropocollagen molecules by the stacking phenomenon is expected to be beneficially affected by the low-gravity environment. We expect this to be due to a more uniform stacking arrangement unbiased by external forces of gravity. Experimental evidence at zero gravity of this supposition is lacking, however, our observations and experience with fibrils formed at one gravity and at hypergravity support its validity.

Regardless of any additional potential benefits to fibrillogenesis itself, we have proved that aggregation of the collagen fibrils at earth gravity results in a density variation from top to bottom of the gel. We have found that this is detrimental to properties which are needed in various biomaterials. For example, artificial corneas and contact lenses formed by the present invention are expected to show improved optical uniformity which results in a much improved product.

The present invention includes the possibility that the collagen gel may be formed from solution in a mold, die or mandrel such that the cast gel will form with a uniform thickness and homogeneous structure. This would be a desirable way to form artificial eye lenses or lens blanks, body tubes such as esophagus and trachea, and other odd shaped parts such as arterial, venous and nerve grafts which are not easily susceptible to formation by cutting and abrading a solid gel sheet or block. Burn treatment foams of collagen may also be formed in space with homogeneous porosity and density.

DESCRIPTION OF THE PREFERRED EMBODIMENTS

As evidence of the inhomogeneity of currently produced collagen gel and partially gelled collagen fibril solutions, several preparations were studied after fibrillogenesis had begun, both under one gravity and at hypergravity. The hypergravity experiment was intended to supply information which, together with the one gravity information, may be extrapolated to zero gravity in lieu of actual data from a zero-gravity environment.

EXAMPLE 1

Lyophilized collagen material was dissolved in 0.05 M acetic acid and buffered with a NaCl/NaOH solution to a final concentration of 0.325% (g/ml) and a pH of about 7.6. The collagen solution was maintained at 4° C. to prevent premature self-assembly of the fibrils.

An aliquot of the solubilized collagen was then placed in a first glass tube (0.5×10 cm) and a second quartz tube (0.6×7.5 cm) and fibrillogeness was initiated by removing the tubes from the ice bath and allowing their temperatures to increase to room temperature (20° C.).

After about 30 minutes the solution became opaque. The first tube was then emptied and samples of the fibril suspension were isolated from the top, the bottom and the middle of the tube. Each sample was analyzed by electron microscopy to determine the fibril density and orientation. The effect of gravity was dramatic in that the very top sample from the tube was devoid of fibrils and the bottom was characterized by a high density of random collagen fibrils. The middle sample contained only a few poorly formed fibrils.

The second tube was scanned in an ISCO UA-5 absorbance monitor with a Type 6 optical unit. The ISCO Type 13 gel scanner was used with a 280-310 nm UV filter. The absorbance monitor gives a reading of the optical density of the material in the tube. A scan along the length of the tube gives a curve, as shown in FIG. 1, of the variation in optical density across the length of the tube. Although the purpose of the invention is to produce a structurally uniform material, we believe that the relationship between structure and optical density is sufficient to use the variation in optical density as an accurate indication of the variation in structure or physical density of the material. In fact, for use of the material as an artificial cornea, uniform optical density would be a very important property itself.

FIG. 1 shows the scan of the second tube at 280 nm where the absorbance increases from the top of the tube to the bottom. The dense portion at the top represents a meniscus and not fibril density.

The slope of the curve between points A and B is 0.061 at a confidence level of 0.97.

The materials in the first and second tubes were therefore inhomogeneous in that the fibril density increased steadily from top to bottom because of gravitational forces on the molecules and fibrils before gelation and the inhomogeneous density and structure leads to other non-uniform properties in the material which detract from its usefulness as a biomaterial.

For comparison, a solution of solubilized collagen such as prepared in this example shows essentially no optical density gradient when scanned immediately after being stirred and poured into a quartz tube. The sedimentation of molecules and fibrils occurs during the fibrillogenesis and before complete gelation.

EXAMPLE 2

A solution of lyophilized collagen was prepared by dissolving the collagen in a 0.15 M acetic acid solution to a concentration of 1.0% (g/ml). This solution was dialyzed at 4° C. against a buffer of NaCl and $K_2PO_4$ and the pH was adjusted to 7.5 with NaOH. Two 0.6×7.5 cm quartz tubes were partially filled with the solution and one tube was placed in a rack on the lab bench and left at room temperature. The second tube was placed in a centrifuge and spun at a rate which produced vectored centrifugal force equal to 3 gravities.

Significant gelation of the one gravity sample began in about 15 minutes, whereas the 3 gravity sample took about 3 hours to reach the same point of gelation.

Figure 3:
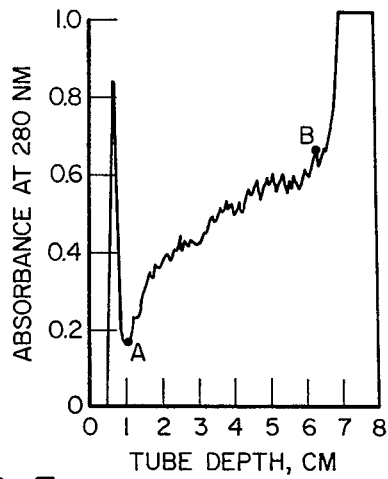
FIG. 3 is a similar graph for a gel reconstituted at three gravities.
Figure 2:
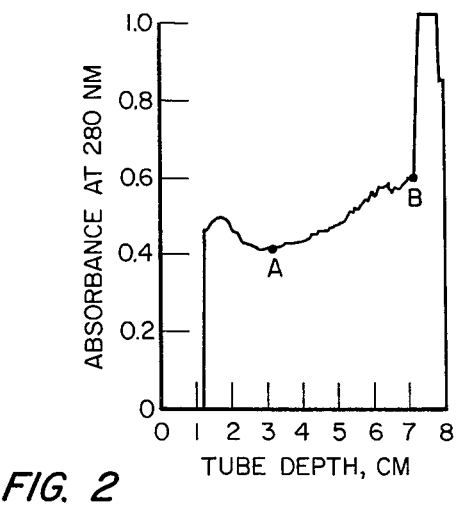

The tubes were scanned after 15 minutes and 3 hours respectively, in the ISCO absorbance monitor to display the optical density gradient in the tubes and provide evidence of the inhomogeneity due to gravitational and centrifugal forces. The absorbance curves are given in FIGS. 2 and 3 for the 1 gravity and 3 gravity tubes, respectively. It can be clearly seen that a much larger gradient in optical density is present in the 3 gravity sample, indicating that fibril density therein is more variable from top to bottom. Quantitatively, the slope from point A to point B in FIG. 2 is 0.054 (r=0.96) and the slope between the same points in FIG. 3 is 0.0872 (r=0.95). The initial high density maximum indicated at the top of the tubes is really a meniscus effect and has been ignored in the slopes.

Extrapolating these results to less than one gravity environments, particularly zero-gravity space environment, it can be readily understood that the density gradients and therefore physical variations in structure due to collagen fibril sedimentation can be reduced if not eliminated by eliminating the forces during fibrillogenesis. In particular, the optical density of the collagen gel can be made very uniform throughout the material, such that a very pure collagen cornea or contact lens can be either cast in substantially final form or cut from large sheets of gel prepared by the inventive process. Lens blanks can be also formed individually or in sheets and can later be further shaped to the desired contour by conventional heating, chemical or pressure treatment.

We claim:

1. A method for production of a homogeneous gel matrix of unique collagen fibrils by the old method of precipitation from a solution comprising solubilized collagen molecules wherein the improvement comprises carrying out the old method under gravitational force of less than one gravity.

2. The method of claim 1, wherein the solution additionally comprises property altering materials selected from carbohydrates and proteins.

3. The method of claim 2, wherein the property altering material is a mucopolysaccharide.

4. The method of claim 1 or 2, wherein the method is carried out under about zero gravity.

5. The method of claim 1, wherein the solution is acidic and the soluble collagen molecules are fibrilized and precipitated by raising the pH above about 7 at a temperature of above about 4° C.

6. The method for production of an individual eye lens blank comprising
   (a) providing a solution comprising solubilized tropocollagen molecules in an eye lens mold, and
   (b) precipitating a homogeneous, self-supporting collagen gel matrix from the solution under gravitational force of less than one gravity.

7. The method for production of an eye lens prosthesis by the method of shaping a lens blank to the desired contour wherein the improvement comprises forming the lens blank by
   (a) providing a thin film of a solution comprising solubilized tropocollagen molecules,
   (b) precipitating a homogeneous, self-supporting gel sheet from the solution under gravitational force of less than one gravity, and
   (c) cutting the eye lens blank from the gel sheet.

* * * * *